(12) United States Patent
Sewake et al.

(10) Patent No.: US 8,715,425 B2
(45) Date of Patent: May 6, 2014

(54) ENDOSCOPE CLEANING/DISINFECTING APPARATUS AND ENDOSCOPE CLEANING/DISINFECTING METHOD

(75) Inventors: Ryuta Sewake, Hachioji (JP); Eiri Suzuki, Sagamihara (JP); Masahiko Tomita, Hachioji (JP); Shinichiro Kawachi, Chofu (JP); Naoya Taya, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 339 days.

(21) Appl. No.: 12/771,360

(22) Filed: Apr. 30, 2010

(65) Prior Publication Data

US 2010/0252074 A1    Oct. 7, 2010

Related U.S. Application Data

(63) Continuation of application No. PCT/JP2009/069400, filed on Nov. 13, 2009.

(30) Foreign Application Priority Data

Dec. 25, 2008    (JP) .................................. 2008-330955

(51) Int. Cl.
*B08B 9/00* (2006.01)
*B08B 9/027* (2006.01)
*A61L 2/00* (2006.01)

(52) U.S. Cl.
USPC ................... 134/22.11; 134/22.1; 134/22.12; 134/26; 134/35; 422/1; 422/2; 422/28

(58) Field of Classification Search
USPC ......... 134/22.1, 22.11, 22.12, 22.18, 26, 228, 134/29, 34, 35, 36; 422/1, 2, 28
See application file for complete search history.

(56) References Cited

U.S. PATENT DOCUMENTS

| | | | |
|---|---|---|---|
| 6,106,691 A * | 8/2000 | Nakamura et al. | ............ 205/701 |
| 6,379,632 B1 * | 4/2002 | Kinoshita et al. | ............ 422/300 |
| 2008/0115814 A1 | 5/2008 | Hasegawa et al. | |
| 2008/0267812 A1 * | 10/2008 | Kawachi et al. | .................. 422/3 |

FOREIGN PATENT DOCUMENTS

| | | |
|---|---|---|
| EP | 0 232 170 A2 | 8/1987 |
| JP | 07-023904 | 1/1995 |
| JP | 2000-126125 | 5/2000 |
| JP | 2005-287581 | 10/2005 |
| JP | 2006-239313 | 9/2006 |

OTHER PUBLICATIONS

Extended Supplementary European Search Report dated Dec. 19, 2012 in European Patent Application No. 09834654.7.

* cited by examiner

*Primary Examiner* — Saeed T Chaudhry (74) *Attorney, Agent, or Firm* — Scully, Scott, Murphy & Presser, P.C.

(57) ABSTRACT

An endoscope cleaning/disinfecting apparatus for processing an endoscope in a cleaning tank using a diluted chemical obtained by diluting a chemical with hot water in a dilution tank of the present invention introduces the hot water into the cleaning tank immediately before processing, introduces the hot water into the dilution tank after the temperature of the hot water introduced into the cleaning tank falls within a specified temperature range, generates the diluted chemical, introduces the diluted chemical into the cleaning tank and processes the endoscope.

2 Claims, 7 Drawing Sheets

ENDOSCOPE CLEANING/DISINFECTING APPARATUS AND ENDOSCOPE CLEANING/DISINFECTING METHOD

CROSS REFERENCE TO RELATED APPLICATION

This application is a continuation application of PCT/JP2009/069400 filed on Nov. 13, 2009 and claims benefit of Japanese Application No. 2008-330955 filed in Japan on Dec. 25, 2008, the entire contents of which are incorporated herein by this reference.

BACKGROUND OF THE INVENTION

1. Field of the Invention

The present invention relates to an endoscope cleaning/disinfecting apparatus and an endoscope cleaning/disinfecting method for disinfecting an endoscope using a diluted chemical diluted with hot water whose water temperature is controlled so as to fall within a predetermined range.

2. Description of the Related Art

As an apparatus for cleaning and disinfecting an endoscope used in the medical field using a chemical, an endoscope cleaning/disinfecting apparatus disclosed in Japanese Patent Application Laid-Open Publication No. 2000-126125 is known.

Among chemicals with which an endoscope is subjected to cleaning processing or disinfecting processing, there are ones which are preferably used within a specified range of temperature higher than room temperature. For example, for an endoscope cleaning/disinfecting apparatus described in Japanese Patent Application Laid-Open Publication No. 2000-126125, it is possible to use a diluted chemical, which is a chemical diluted with hot water supplied from a hot water supply source such as a hot water supply system.

SUMMARY OF THE INVENTION

An endoscope cleaning/disinfecting apparatus of the present invention is an endoscope cleaning/disinfecting apparatus that processes an endoscope using a diluted chemical obtained by diluting a chemical with hot water whose water temperature is controlled so as to fall within a predetermined specified temperature range, including a first conduit connected to a hot water supply source that supplies the hot water, a branch conduit that branches off from the first conduit in two directions, a cleaning tank that can accommodate the endoscope, a dilution tank that mixes the hot water and the chemical, a second conduit that connects one end of the branch conduit and the cleaning tank, a third conduit that connects the other end of the branch conduit and the dilution tank, a branch selection section that can select one or a plurality of states of the branch conduit from among a state in which the first conduit is in communication with the second conduit, a state in which the first conduit is in communication with the third conduit and a state in which the second conduit is in communication with the third conduit, a first temperature measuring section that measures a temperature of the liquid introduced into the cleaning tank via the second conduit and a control section that controls operation of the branch selection section, thereby causes the first conduit to communicate with the second conduit, introduces the hot water into the cleaning tank, causes the first conduit to communicate with the third conduit after the measurement result of the first temperature measuring section falls within the specified temperature range, introduces the hot water into the dilution tank and generates the diluted chemical.

Furthermore, an endoscope cleaning/disinfecting method of the present invention is an endoscope cleaning/disinfecting method using an endoscope cleaning/disinfecting apparatus including a first conduit connected to a hot water supply source that supplies hot water whose temperature is controlled so as to fall within a predetermined specified temperature range, a branch conduit that branches off from the first conduit in two directions, a cleaning tank that can accommodate the endoscope, a dilution tank that mixes the hot water and a chemical to obtain a diluted chemical, a second conduit that connects one end of the branch conduit and the cleaning tank, a third conduit that connects the other end of the branch conduit and the dilution tank, a branch selection section that can select one or a plurality of states of the branch conduit from among a state in which the first conduit is in communication with the second conduit, a state in which the first conduit is in communication with the third conduit and a state in which the second conduit is in communication with the third conduit and a first temperature measuring section that measures a temperature of the liquid introduced into the cleaning tank via the second conduit, the method including a step of introducing the hot water into the cleaning tank in a state in which the first conduit is in communication with the second conduit, and a step of causing the first conduit to communicate with the third conduit after the measurement result of the first temperature measuring section falls within the specified temperature range, introducing the hot water into the dilution tank and generating the diluted chemical.

DETAILED DESCRIPTION OF THE PREFERRED EMBODIMENT(S)

Preferred embodiments of an endoscope cleaning/disinfecting apparatus according to the present invention will be described with reference to the accompanying drawings. In the drawings used in the following descriptions, scaling is made to differ from one component to another to illustrate the respective components on the order of size recognizable on the drawings, and the present invention is not limited only to the quantity of the components, shapes of the components, ratio in size of the components and relative positional relationship between the components described in the drawings.

First Embodiment

Figure 1:
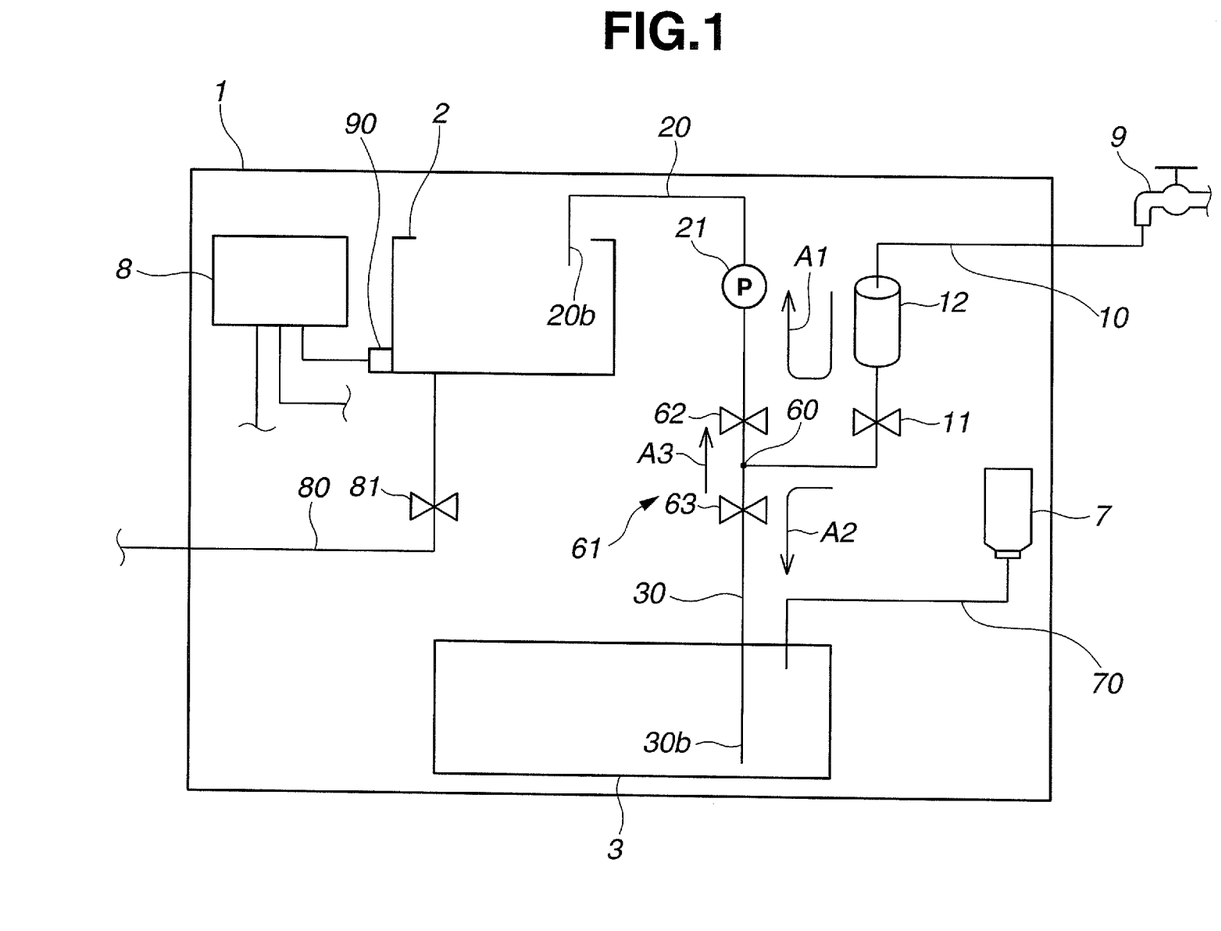
FIG. 1 is a diagram illustrating a schematic configuration of an endoscope cleaning/disinfecting apparatus according to a first embodiment.
Figure 2:
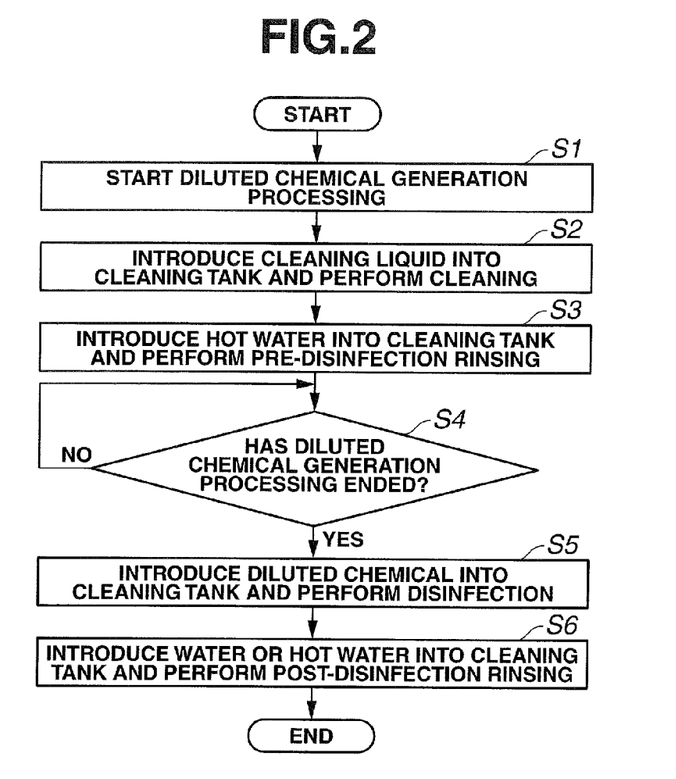
FIG. 2 is a flowchart illustrating the operation of the endoscope cleaning/disinfecting apparatus according to the first embodiment.
Figure 3:
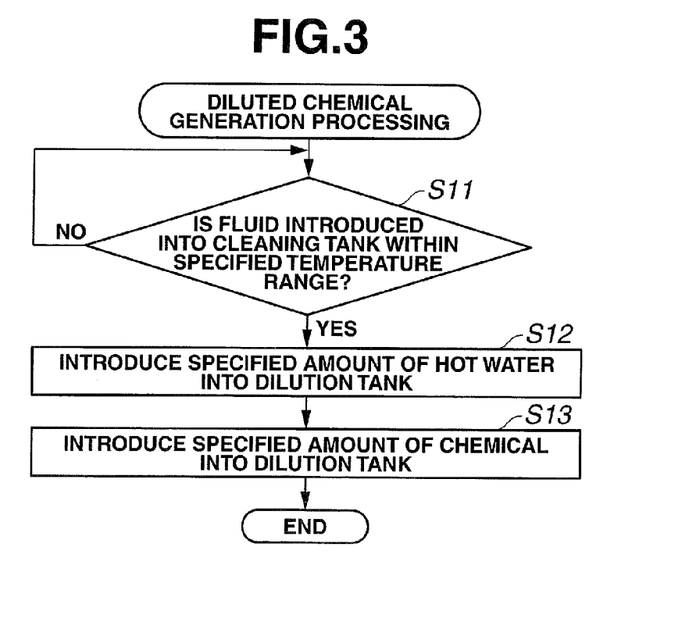
FIG. 3 is a flowchart of diluted chemical generation processing.

Hereinafter, a first embodiment of the present invention will be described. FIG. 1 is a diagram illustrating a schematic configuration of an endoscope cleaning/disinfecting apparatus according to a first embodiment. FIG. 2 is a flowchart illustrating the schematic operation of the endoscope cleaning/disinfecting apparatus according to the first embodiment. FIG. 3 is a flowchart of diluted chemical generation processing.

The endoscope cleaning/disinfecting apparatus 1 of the present embodiment is configured by including a cleaning tank 2, a dilution tank 3, a chemical storing section 7, a control section 8 and a plurality of conduits and valves, details of which will be described later. When described schematically, the endoscope cleaning/disinfecting apparatus 1 is an apparatus that dilutes a chemical stored in the chemical storing section 7 with hot water supplied from a hot water supply source 9 provided outside the apparatus in the dilution tank 3 to generate a diluted chemical and performs cleaning processing and disinfecting processing on an endoscope using the diluted chemical in the cleaning tank 2.

Here, the hot water supplied from the hot water supply source 9 to the endoscope cleaning/disinfecting apparatus 1 refers to water whose water temperature is controlled so as to fall within a specified temperature range, which is a predetermined temperature range. The specified temperature range of hot water is within a range suitable for performing cleaning processing or disinfecting processing on the endoscope using the diluted chemical and is preferably within a range that will exert no influence such as deformation on the endoscope cleaning apparatus 1 and the components of the endoscope.

Therefore, though the specified temperature range of hot water is not particularly limited, the specified temperature is set, for example, to a room temperature (20° C.) or above and 80° C. or below. Hereinafter, a case will be described as an example where the specified range of hot water is 30° C. or above and 60° C. or below.

One end of a first conduit 10 of the endoscope cleaning/disinfecting apparatus 1 is connected to the hot water supply source 9. The first conduit 10 is provided with a first valve 11 that opens/closes the first conduit 10 and a filter apparatus 12 that filters hot water that flows through the first conduit 10.

Although FIG. 1 shows a mode in which the first conduit 10 is provided with the filter apparatus 12 and the first valve 11 in that order from the hot water supply source 9 side, the order of arrangement of the first valve 11 and the filter apparatus 12 may be reverse to this order. Furthermore, the filter apparatus 12 may also be disposed outside the endoscope cleaning/disinfecting apparatus 1.

A branch conduit 60 that branches off in two directions (three directions when the first conduit is included) is disposed at the other end opposite to the one end connected to the hot water supply source 9 of the first conduit 10. One end of a second conduit 20 and one end of a third conduit 30 are connected to the branch conduit 60.

The other end 20b of the second conduit 20 is connected to the cleaning tank 2. The cleaning tank 2 is a container that can accommodate an endoscope (not shown) therein. An exhaust conduit 80 that connects the cleaning tank 2 and the outside of the endoscope cleaning/disinfecting apparatus 1 is connected to the bottom surface portion of the cleaning tank 2. An exhaust valve 81 is disposed on the exhaust conduit 80 and a liquid in the cleaning tank 2 can be exhausted to the outside of the endoscope cleaning/disinfecting apparatus 1 by leaving the exhaust valve 81 open. The liquid may be exhausted from the cleaning tank 2 by gravity or by a pump.

The cleaning tank 2 is provided with a first temperature measuring section 90 that measures the temperature of the wall surface of the cleaning tank 2. The first temperature measuring section 90 can derive the temperature of the fluid introduced from the other end 20b of the second conduit 20 into the cleaning tank 2 from the measurement result of the temperature of the wall surface of the cleaning tank 2. The first temperature measuring section 90 may be disposed at the other end 20b of the second conduit 20 and configured to directly measure the temperature of the fluid introduced from the other end 20b of the second conduit 20 into the cleaning tank 2. Furthermore, the cleaning tank 2 is provided with a liquid level detection sensor (not shown) that can detect the height of the liquid level in the cleaning tank 2 and can detect the amount of the liquid introduced into the cleaning tank 2.

The other end 30b of the third conduit 30 is connected to the dilution tank 3. The dilution tank 3 is a hollow container. In the dilution tank 3, the other end 30b of the third conduit 30 is disposed in the vicinity of the bottom surface of the dilution tank 3 and can suction the liquid in the dilution tank 3 via the third conduit 30. Furthermore, the dilution tank 3 is provided with a liquid level detection sensor that can detect the height of the liquid level in the dilution tank 3 and can detect the amount of the liquid introduced into the dilution tank 3.

The chemical storing section 7 that stores a chemical is connected to the dilution tank 3 via the chemical transfer conduit 70 and it is possible to generate a diluted chemical by diluting the chemical with the liquid introduced from the third conduit 30 in the dilution tank 3. A plurality of types of chemical may be used as the chemical stored in the chemical transfer conduit 70 and diluted in the dilution tank 3.

The second conduit 20 is provided with a first pump 21 that transfers the fluid to the other end 20b side of the second conduit 20 and a second valve 62 that opens/closes the second conduit 20. Furthermore, the third conduit 30 is provided with a third valve 63 that opens/closes the third conduit 30.

When, for example, the second valve 62 is assumed to be left open and the third valve 63 is assumed to be closed, the first conduit 10 is in communication with the second conduit 20 out of the first conduit 10, the second conduit 20 and the third conduit 30. On the other hand, when the second valve 62 is assumed to be closed and the third valve 63 is assumed to be left open, the first conduit 10 is in communication with the third conduit 30. Furthermore, when both the second valve 62 and the third valve 63 are assumed to be left open, the second conduit 20 is in communication with the third conduit 30.

As described above, the second valve 62 and the third valve 63 of the present embodiment constitute a branch selection section 61 which can select one or a plurality of states from among a state in which the first conduit 10 is in communication with the second conduit 20, a state in which the first conduit 10 is in communication with the third conduit 30 and a state in which the second conduit 20 is in communication with the third conduit 30. Such a branch selection section 61 can also be realized by disposing, for example, a three-way valve on the branch conduit 60.

The control section 8 is an apparatus that controls operations of the above described sections of the endoscope cleaning/disinfecting apparatus 1 based on a predetermined program and is made up of a computer configured by including, for example, an arithmetic apparatus, a storage apparatus and an input/output apparatus.

To be more specific, the control section 8 is electrically connected to the first valve 11, the second valve 62, the third valve 63, the exhaust valve 81 and the first pump 21 and can control operations of these valves and the first pump 21. Furthermore, the control section 8 is electrically connected to the first temperature measuring section 90, the liquid level detection sensor of the cleaning tank 2 and the liquid level detection sensor of the dilution tank 3 and can receive measurement results outputted from the first temperature measuring section 90 and the liquid level detection sensor.

The operation of the endoscope cleaning/disinfecting apparatus 1 configured as shown above will be described with reference to flowcharts shown in FIG. 2 and FIG. 3. The operation described below will be controlled by the control section 8.

First, diluted chemical generation processing, which is a subroutine, starts in step S1 and moves to step S2. That is, the diluted chemical generation processing is executed in parallel with processing from step S2 onward.

The diluted chemical generation processing shown in the flowchart in FIG. 3 is processing for generating a diluted chemical in the dilution tank 3 to be used for disinfecting processing in step S5, which will be described later. Even when started, the diluted chemical generation processing remains on standby when the temperature of the fluid introduced into the cleaning tank 2 is outside a specified temperature range as shown in step S11, and step S12 is executed when the temperature of the fluid introduced into the cleaning tank 2 falls within the specified temperature range. Here, the temperature of the fluid introduced into the cleaning tank 2 is derived from the measurement result of the first temperature measuring section 90 as described above.

In step S12, the first valve 11 and the third valve 63 are left open and the first conduit 10 is made to be in communication with the third conduit 30. Thus, hot water supplied from the hot water supply source 9 is introduced into the dilution tank 3 (arrow A2 in FIG. 1). After a specified amount of hot water is stored in the dilution tank 3, the third valve 63 is closed and the introduction of hot water into the dilution tank 3 is stopped.

At the start of execution of step S12, if the first valve 11 is open, the first valve 11 is kept open. Furthermore, during execution of step S12, the operation of the second valve 62 can be controlled under instructions from other processing.

In step S13, a specified amount of chemical is introduced into the dilution tank 3 from the chemical storing section 7 via the chemical transfer conduit 70. As a result, a diluted chemical which is a mixture of the chemical and hot water at a specified ratio is generated in the dilution tank 3. This is the end of the diluted chemical generation processing.

Furthermore, the present proposal is not limited to the flow in FIG. 3 and hot water may be introduced after introducing the chemical into the dilution tank beforehand or hot water and the chemical may be introduced in parallel. However, it is preferable to introduce the chemical after introducing hot water as in the flow shown in FIG. 3 because a high concentration chemical does not directly contact the dilution tank in this way.

On the other hand, in step S2 shown in FIG. 2, cleaning processing is performed whereby a cleaning liquid is introduced from a cleaning liquid supply section (not shown) into the cleaning tank 2 and the endoscope accommodated in the cleaning tank 2 is cleaned with the cleaning liquid. After performing the cleaning processing for a predetermined time, the exhaust valve 81 is left open and the cleaning liquid in the cleaning tank 2 is exhausted from the exhaust conduit 80. After the exhaust valve 81 is closed, the process moves to step S3.

Next, in step S3, the first conduit 10 is made to be in communication with the second conduit 20 by leaving the first valve 11 and the second valve 62 open. By introducing a predetermined amount of hot water into the cleaning tank 2 as shown by the arrow A1 in FIG. 1, pre-disinfection rinsing processing is performed whereby the interior of the cleaning tank 2 is rinsed with hot water.

The hot water used for the pre-disinfection rinsing processing is exhausted from the exhaust conduit 80 by leaving the exhaust valve 81 open. The pre-disinfection rinsing processing in step S3 may be performed a plurality of times by repeating the introduction of hot water into the cleaning tank 2 and exhausting of hot water from the inside of the cleaning tank 2. After the pre-disinfection rinsing processing ends, the exhaust valve 81 is closed and the process then moves to step S4.

Since hot water at a water temperature within a specified temperature range supplied from the hot water supply source 9 is introduced into the cleaning tank 2 via the second conduit 20 through the pre-disinfection rinsing processing in step S3, the temperature of the fluid measured by the first temperature measuring section 90 and introduced into the cleaning tank 2 changes within the specified temperature range. That is, in the present embodiment, step S12 in the aforementioned diluted chemical generation processing starts during the pre-disinfection rinsing processing in step S3.

Next, it is judged in step S4 whether or not the diluted chemical generation processing has ended. When the diluted chemical generation processing has not ended, the process waits to confirm the end of the dilution processing generation processing and then moves to step S5. When the end of the dilution processing generation processing is not confirmed even after a lapse of a predetermined time, such a configuration may be adopted that the operation is stopped after displaying a warning or outputting a warning sound or the like.

In step S5, the first valve 11 is closed and the second valve 62 and the third valve 63 are left open. By causing, the first pump 21 to operate, the diluted chemical stored in the dilution tank 3 is transferred to the cleaning tank 2 via the third conduit 30 and the second conduit 20 as shown by an arrow A3 in FIG. 1 and disinfecting processing is then performed whereby the endoscope accommodated in the cleaning tank 2 is disinfected.

After performing the disinfecting processing for a predetermined time, the exhaust valve 81 is left open and the diluted chemical in the cleaning tank 2 is exhausted from the exhaust conduit 80. After the exhaust valve 81 is closed, the process moves to step S6.

Next, in step S6, the first valve 11 and the second valve 62 are left open, the first conduit 10 is made to be in communication with the second conduit 20, hot water supplied from the hot water supply source 9 is introduced into the cleaning tank 2 as shown by the arrow A1 in FIG. 1 and post-disinfection rinsing processing is performed whereby the interior of the cleaning tank 2 is rinsed with hot water. The hot water used for the post-disinfection rinsing processing is exhausted from the exhaust conduit 80 by leaving the exhaust valve 81 open. The post-disinfection rinsing processing in step S6 may be performed a plurality of times by repeating the introduction and exhausting of hot water. After the post-disinfection rinsing processing ends, the exhaust valve 81 is closed.

This is the end of the operation of endoscope cleaning and disinfection using the endoscope cleaning/disinfecting apparatus 1 according to the present embodiment. When cleaning and disinfection of the endoscope are repeatedly performed, the process returns to step S1 and the above described operation is repeated.

As described above, according to the present embodiment, hot water is introduced into the cleaning tank 2 via the first conduit 10 and the second conduit 20 in the pre-disinfection rinsing processing in step S3 prior to the introduction of hot water into the dilution tank 3.

Here, before the pre-disinfection rinsing processing in step S3 is performed, since the supply of hot water from the hot water supply source 9 to the endoscope cleaning/disinfecting apparatus 1 is stopped, the temperatures of the conduits and filter apparatus 12 in the endoscope cleaning/disinfecting apparatus 1 and the temperature of the liquid remaining in the conduits and filter apparatus 12 are lower than the temperature of hot water (30° C. or above, 60° C. or below in the present embodiment).

Therefore, even if hot water at a temperature within a specified temperature range is supplied from the hot water supply source 9, the liquid remaining in the conduits and filter apparatus 12 is made to flow and the temperature of hot water introduced into the cleaning tank 2 or dilution tank 3 is lower than the specified temperature range until the temperatures of the conduits and filter apparatus 12 reach the vicinity of the specified temperature range.

However, according to the endoscope cleaning/disinfecting apparatus 1 of the present embodiment, the temperature of hot water introduced into the cleaning tank 2 in the pre-disinfection rinsing processing in step S3 falls within the specified temperature range and hot water is then introduced into the dilution tank 3. Furthermore, according to the present embodiment, by using hot water in the pre-disinfection rinsing processing in step S3, the wall surface of the cleaning tank 2 is also heated to within the specified temperature range.

That is, the present embodiment obtains a diluted chemical diluted with hot water within a specified temperature range, which is a temperature suitable for disinfecting the endoscope at the start of the disinfecting processing in step S5 and the wall surface of the cleaning tank 2 subjected to disinfecting processing with a diluted chemical is heated to within the specified temperature range.

Therefore, the endoscope cleaning/disinfecting apparatus 1 of the present embodiment need not heat the diluted chemical and the cleaning tank 2 using a heater or the like in the disinfecting processing in step S5 and can save a waiting time for heating, so can thereby shorten the time necessary to perform disinfecting processing.

Furthermore, since the introduction of hot water into the dilution tank 3 in step S12 of the diluted chemical generation processing is performed in parallel with pre-disinfection rinsing processing, it is possible to shorten or eliminate the waiting time until the generation of the diluted chemical in step S4 is completed and further shorten the time necessary for cleaning processing and disinfecting processing of the endoscope using the endoscope cleaning/disinfecting apparatus 1.

A case has been described in the aforementioned present embodiment where hot water is assumed not to be used in the cleaning processing in step S2, but such a configuration may also be adopted that hot water from the hot water supply source 9 is used for the cleaning processing in step S2.

In this case, since the temperature of the liquid introduced into the cleaning tank 2 reaches within the specified temperature range in the execution of the cleaning processing in step S2, the introduction of hot water into the dilution tank 3 in the diluted liquid generation processing (step S12) starts during the cleaning processing. This makes it easier to further shorten or eliminate the waiting time until the generation of the diluted chemical in step S4 is completed.

Furthermore, since detergency of the cleaning liquid generally increases as the temperature rises, it is also possible to shorten the time necessary for cleaning processing.

Second Embodiment

Figure 4:
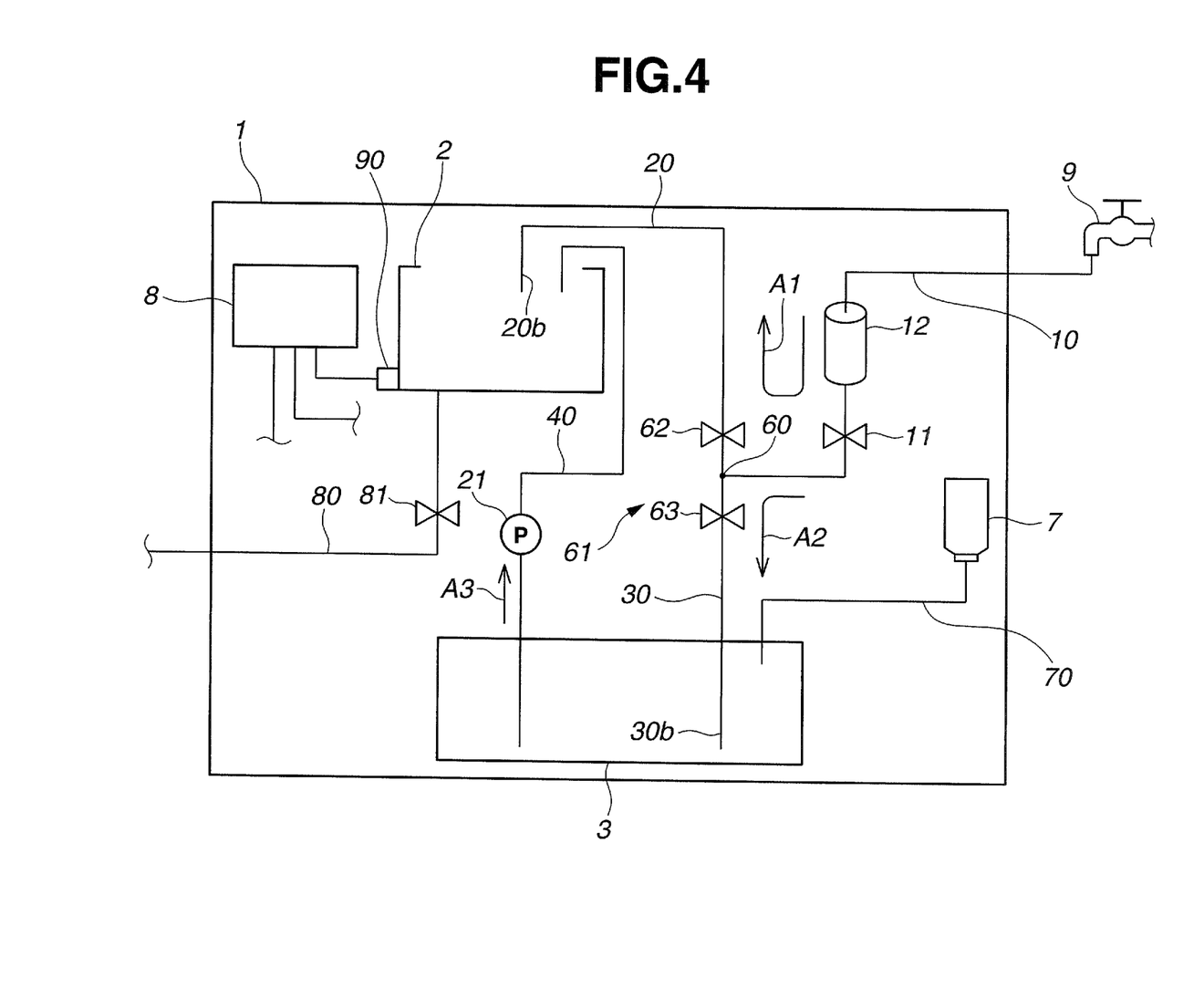
FIG. 4 is a diagram illustrating a schematic configuration of an endoscope cleaning/disinfecting apparatus according to a second embodiment.

Hereinafter, a second embodiment of the present invention will be described. FIG. 4 is a diagram illustrating a schematic configuration of an endoscope cleaning/disinfecting apparatus according to the second embodiment.

The second embodiment is different from the first embodiment in a mode of transfer of a diluted chemical from the dilution tank 3 to the cleaning tank 2. Hereinafter, suppose only the differences from the first embodiment will be described and components similar to those of the first embodiment will be assigned the same reference numerals and descriptions thereof will be omitted as appropriate.

In the present embodiment, a fourth conduit 40 is disposed which is connected to the dilution tank 3 and the cleaning tank 2 and the first pump 21 is disposed on the fourth conduit 40. Therefore, in the disinfecting processing in step S5, operating the first pump 21 causes the diluted chemical stored in the dilution tank 3 to be transferred to the cleaning tank 2 via the fourth conduit 40 as shown by an arrow A3.

Third Embodiment

Figure 5:
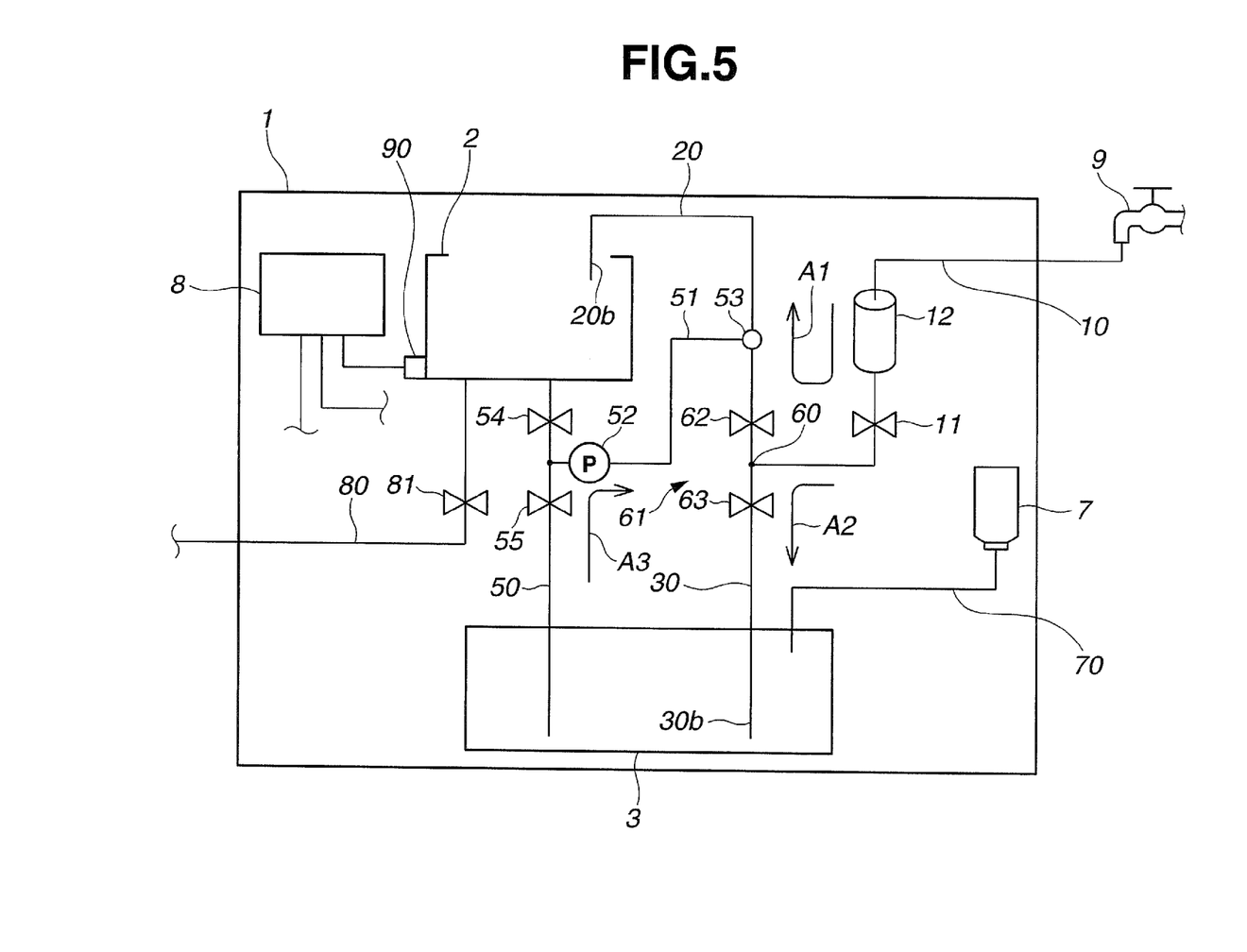
FIG. 5 is a diagram illustrating a schematic configuration of an endoscope cleaning/disinfecting apparatus according to a third embodiment.

Hereinafter, a third embodiment of the present invention will be described. FIG. 5 is a diagram illustrating a schematic configuration of an endoscope cleaning/disinfecting apparatus according to the third embodiment.

The third embodiment is different from the first embodiment in a mode of transfer of a diluted chemical from the dilution tank 3 to the cleaning tank 2. Hereinafter, suppose only the differences from the first embodiment will be described and components similar to those of the first embodiment will be assigned the same reference numerals and descriptions thereof will be omitted as appropriate.

The present embodiment provides a fifth conduit 50 connected to the bottom surface of the cleaning tank 2 and the dilution tank 3 and a sixth conduit 51 that branches off from the fifth conduit 50 and is connected to the second conduit 20. A fourth valve 54 is disposed on the fifth conduit 50 closer to the cleaning tank 2 side than the branch to the sixth conduit 51 and a fifth valve 55 is disposed closer to the dilution tank 3 side than the branch to the sixth conduit 51.

The sixth conduit 51 is provided with a second pump 52 that transfers a fluid from the fifth conduit 50 side to the second conduit 20 side in the sixth conduit 51. A three-way valve 53 is disposed in a joint portion between the sixth conduit 51 and the second conduit 20.

The three-way valve 53 is configured such that it is possible to switch, under instructions from the control section, between a state in which the second conduit 20 on the cleaning tank 2 side is in communication with that on the branch conduit 60 side and a state in which the second conduit on the cleaning tank 2 side is in communication with the sixth conduit 51.

The endoscope cleaning/disinfecting apparatus configured as shown above performs the cleaning processing in step S2 with the fourth valve 54 closed.

Furthermore, in the pre-disinfection rinsing processing in step S3, the fourth valve 54 and the fifth valve 55 are closed first and the three-way valve 53 is set so that the second conduit 20 on the cleaning tank 2 side is made to be in communication with that on the branch conduit 60 side and hot water is introduced into the cleaning tank 2 as shown by an arrow A1. Next, after a predetermined amount of hot water is introduced into the cleaning tank 2, the first valve 11 is closed to stop the supply of hot water and the three-way valve 53 is set so that the second conduit on the cleaning tank 2 side is made to be in communication with the sixth conduit 51. The fourth valve 54 is then left open and the second pump 52 is made to operate so as to cause hot water in the cleaning tank 2 to circulate via the sixth conduit 51 and the second conduit 20.

In the disinfecting processing in step S5, the fourth valve 54 is closed, the fifth valve 55 is left open and the three-way valve 53 is set so that the second conduit on the cleaning tank 2 side is made to be in communication with the sixth conduit 51. By causing the second pump 52 to operate, the diluted chemical in the dilution tank 3 is introduced into the cleaning tank 2 via the fifth conduit 50, the sixth conduit 51 and the second conduit 20 as shown by an arrow A3.

The present embodiment causes hot water to circulate via the second conduit 20 and the sixth conduit 51 in the pre-disinfection rinsing processing in step S3, and can thereby cause the temperatures of the second conduit 20 and the sixth conduit 51 to approximate to the temperature of hot water and prevent the temperature of the diluted chemical from falling when the diluted chemical is transferred from the dilution tank 3 to the cleaning tank 2.

Fourth Embodiment

Figure 6:
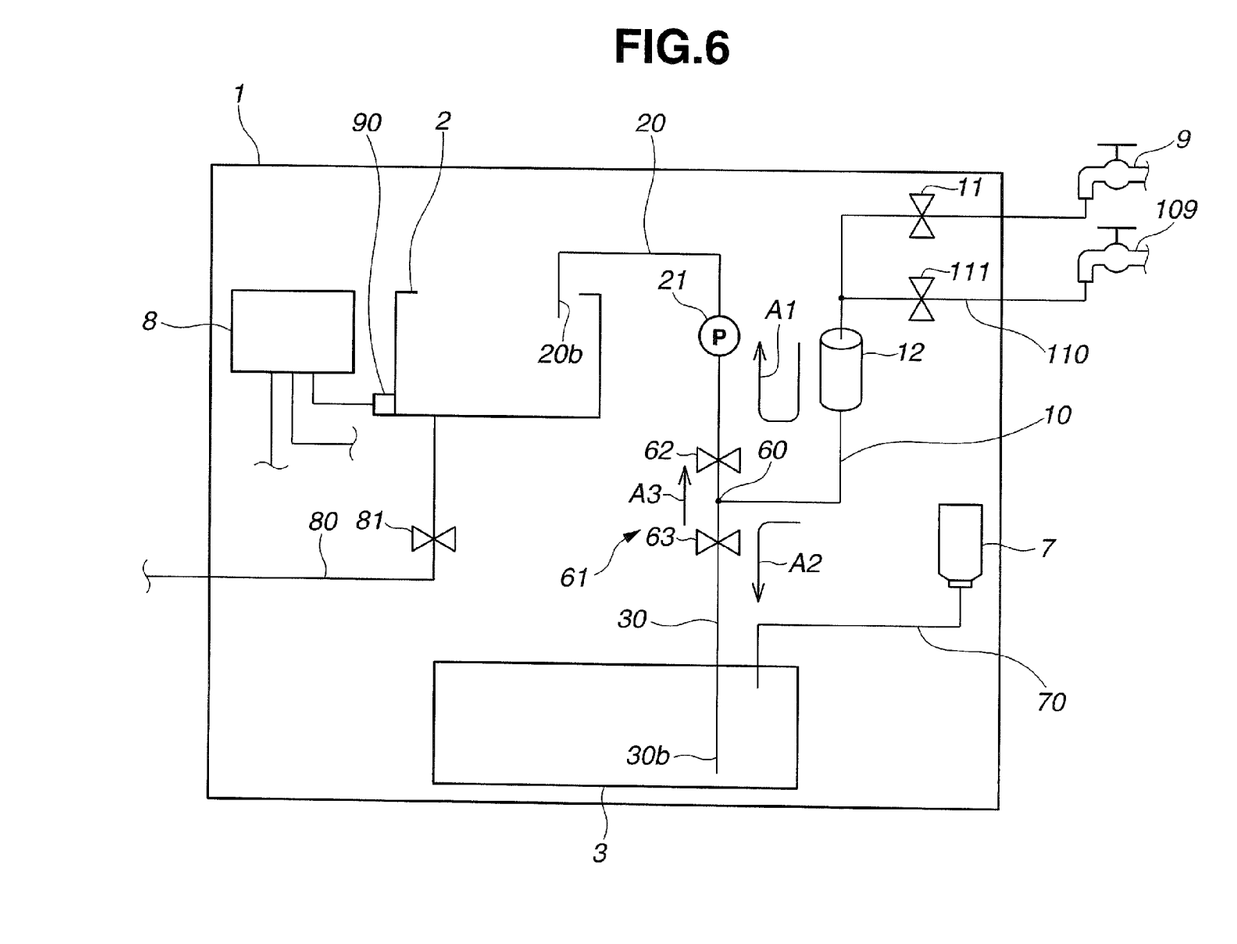
FIG. 6 is a diagram illustrating a schematic configuration of an endoscope cleaning/disinfecting apparatus according to a fourth embodiment.
Figure 7:
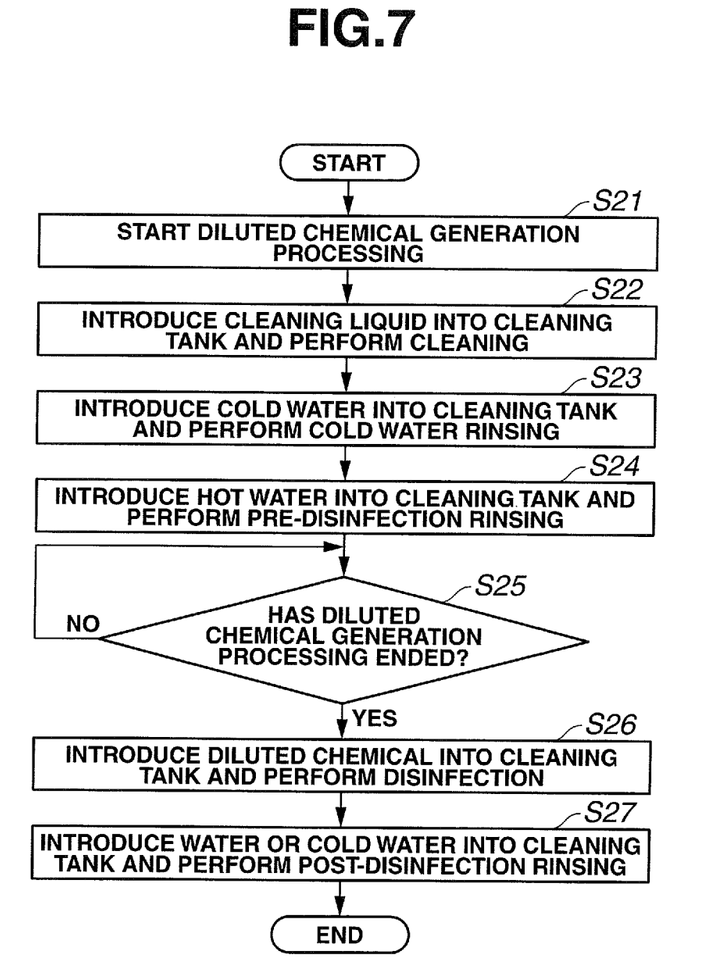
FIG. 7 is a flowchart illustrating the operation of the endoscope cleaning/disinfecting apparatus according to the fourth embodiment.

Hereinafter, a fourth embodiment of the present invention will be described. FIG. 6 is a diagram illustrating a schematic configuration of an endoscope cleaning/disinfecting apparatus according to a fourth embodiment. FIG. 7 is a flowchart illustrating the operation of the endoscope cleaning/disinfecting apparatus according to the fourth embodiment.

The fourth embodiment is different from the first embodiment in that water whose temperature is not controlled is made to be available for cleaning processing and rinsing processing. Hereinafter, suppose only the differences from the first embodiment will be described and components similar to those of the first embodiment will be assigned the same reference numerals and descriptions thereof will be omitted as appropriate. Furthermore, suppose water whose temperature is not controlled is referred to as "cold water" unlike hot water for convenience in the sense that its temperature is low compared to hot water.

In the present embodiment, one end of a cold water conduit 110 is connected to a cold water supply source 109 that supplies cold water and the other end thereof is connected to the first conduit 10. The cold water conduit 110 is provided with a cold water valve 111 for opening/closing the cold water conduit 110 and controlling the supply of cold water.

Although a case will be described in the present embodiment shown in FIG. 6 where the cold water conduit 110 is connected to the first conduit 10 as an example, any configuration is acceptable as long as cold water can be introduced into the cleaning tank 2. For example, such a configuration may be adopted that the other end of the cold water conduit 110 is connected to the second conduit 20 or such a configuration may be adopted that the other end of the cold water conduit 110 is disposed in the cleaning tank 2.

The operation of the endoscope cleaning/disinfecting apparatus according to the present embodiment configured as shown above will be described with reference to the flowchart shown in FIG. 7.

First, in step S21, diluted chemical generation processing, which is a subroutine, is started and the process moves to step S22. Since the diluted chemical generation processing is similar to that of the first embodiment, descriptions thereof will be omitted.

Next, in step S22, a cleaning liquid is introduced from a cleaning liquid supply section (not shown) into the cleaning tank 2 and cleaning processing is performed whereby the endoscope accommodated in the cleaning tank 2 is cleaned with a cleaning liquid. After performing cleaning processing for a predetermined time, the exhaust valve 81 is left open and the cleaning liquid in the cleaning tank 2 is exhausted from the exhaust conduit 80. After the exhaust valve 81 is closed, the process moves to step S23.

Next, in step S23, the cold water valve 111 and the second valve 62 are left open and the third valve 63 is closed so that the first conduit 10 is made to be in communication with the second conduit 20. By introducing a predetermined amount of cold water into the cleaning tank 2 as shown by an arrow A1 in FIG. 6, cold water rinsing processing is performed whereby the interior of the cleaning tank 2 is rinsed with cold water.

The cold water used for the cold water rinsing processing is exhausted from the exhaust conduit 80 by leaving the exhaust valve 81 open. The cold water rinsing processing in step S23 may be performed a plurality of times by repeating the introduction and exhausting of cold water. After the cold water rinsing processing ends, the exhaust valve 81 is closed and the process then moves to step S24.

Next, in step S24, with the first valve 11 left open, a predetermined amount of hot water is introduced into the cleaning tank 2 via the first conduit 10 and the second conduit 20 as shown by the arrow A1 in FIG. 1, and pre-disinfection rinsing processing is performed.

Here, as in the case of the first embodiment, since the temperature of the fluid measured by the first temperature measuring section 90 and introduced into the cleaning tank 2 rises to within a specified temperature range, step S12 of diluted chemical generation processing starts during the pre-disinfection rinsing processing.

Next, it is judged in step S25 whether or not the diluted chemical generation processing has ended. When the diluted chemical generation processing has not ended, the process waits to confirm the end of the dilution processing generation processing and then moves to step S26. When the end of the dilution processing generation processing cannot be confirmed after a lapse of a predetermined time, such a configuration may be adopted that the operation is stopped after displaying a warning or outputting a warning sound or the like.

In step S26, as in the case of step S5 of the first embodiment, the first valve 11 is closed, and the second valve 62 and the third valve 63 are left open. By causing the first pump 21 to operate, the diluted chemical stored in the dilution tank 3 is transferred to the cleaning tank 2 via the third conduit 30 and the second conduit 20 as shown by an arrow A3 in FIG. 6 and disinfecting processing is performed whereby the endoscope accommodated in the cleaning tank 2 is disinfected.

After performing the disinfecting processing for a predetermined time, the exhaust valve 81 is left open and the diluted chemical in the cleaning tank 2 is exhausted from the exhaust conduit 80. After the exhaust valve 81 is closed, the process moves to step S27.

Next, in step S27, with the cold water valve 111 and the second valve 62 left open and the third valve 63 closed, a predetermined amount of cold water is introduced into the cleaning tank 2 as shown by the arrow A1 in FIG. 6 and post-disinfection rinsing processing is performed whereby the interior of the cleaning tank 2 is rinsed with cold water.

The cold water used for the post-disinfection rinsing processing is exhausted from the exhaust conduit 80 by leaving the exhaust valve 81 open. The post-disinfection rinsing processing in step S27 may be performed a plurality of times by repeating the introduction and exhausting of cold water. After the post-disinfection rinsing processing ends, the exhaust valve 81 is closed.

This is the end of the operation of the cleaning processing and the disinfecting processing on the endoscope using the endoscope cleaning/disinfecting apparatus according to the present embodiment. When the cleaning processing and the disinfecting processing on the endoscope are repeatedly performed, the process returns to step S21 and the above described operation is repeated.

As described above, the present embodiment is different from the first embodiment in that cold water is used as part of the rinsing processing before and after the disinfecting processing, but the present embodiment is similar to the first embodiment in that hot water is introduced into the cleaning tank 2 in the pre-disinfection rinsing processing in step S24 prior to the introduction of hot water into the dilution tank 3.

Thus, the present embodiment can reduce the consumption of hot water whose temperature is controlled compared to the first embodiment and reduce the energy necessary for the cleaning processing and disinfecting processing on the endoscope. The other effects are similar to those of the first embodiment.

Fifth Embodiment

Figure 8:
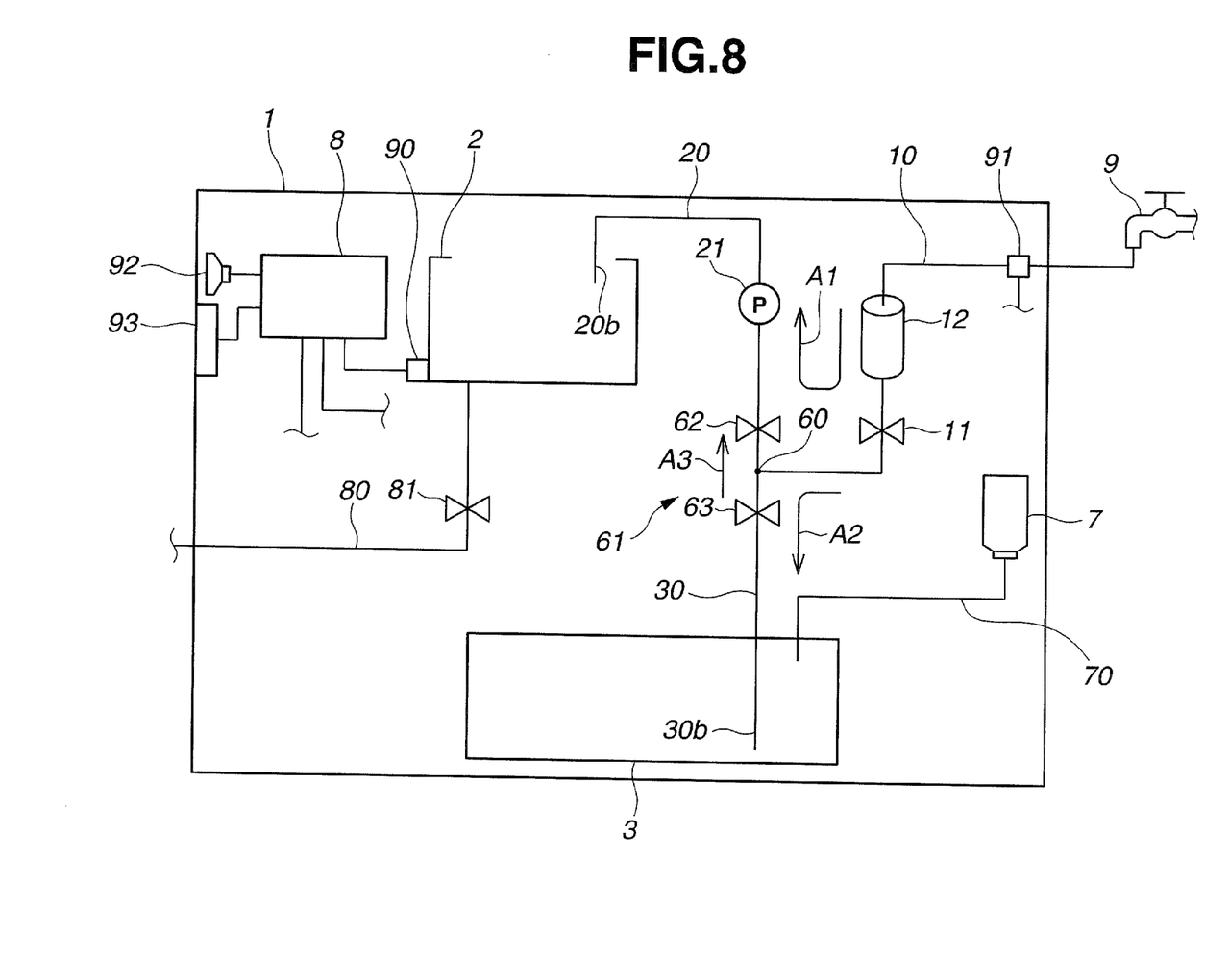
FIG. 8 is a diagram illustrating a schematic configuration of an endoscope cleaning/disinfecting apparatus according to a fifth embodiment.

Hereinafter, a fifth embodiment of the present invention will be described. FIG. 8 is a diagram illustrating a schematic configuration of an endoscope cleaning/disinfecting apparatus according to a fifth embodiment.

Hereinafter, suppose only the differences from the first embodiment will be described and components similar to those of the first embodiment will be assigned the same reference numerals and descriptions thereof will be omitted as appropriate.

In the present embodiment, as shown in FIG. 8, the first conduit 10 is provided with a second temperature measuring section 91 that measures the temperature of the fluid in the first conduit 10. Furthermore, a speaker 92 and a display apparatus 93 are provided, which are information output apparatuses for transmitting information to the user. The second temperature measuring section 91, the speaker 92 and the display apparatus 93 are electrically connected to the control section 8.

When the temperature of hot water measured by the second temperature measuring section 91 exceeds an upper limit value, which is a predetermined value, the control section 8 of the endoscope cleaning/disinfecting apparatus 1 of the present embodiment closes the first valve 11, outputs a warning sound through the speaker 92 and displays a warning through the display apparatus 93.

Here, the upper limit value of the temperature of hot water is set to a temperature that may cause influences such as deformation of the endoscope cleaning apparatus 1 and components of the endoscope or a temperature exceeding a range within which the chemical can be used, whichever is the lower.

According to the present embodiment described above, it is possible to prevent hot water at a temperature that has an adverse influence on the endoscope cleaning apparatus 1 and components of the endoscope or chemical from flowing into the endoscope cleaning/disinfecting apparatus 1.

The second temperature measuring section 91 may also be configured to be disposed closer to the branch conduit 60 side than the first valve 11 of the first conduit 10. Furthermore, adopting a configuration in which the second temperature measuring section 91 is not disposed and the first valve 11 is closed when the measurement result of the first temperature measuring section 90 exceeds an upper limit value can also prevent the endoscope cleaning apparatus 1 and the components of the endoscope or chemical from being exposed to hot water at a temperature equal to or higher than the upper limit value for a long time. In this case, it is preferable to adopt a configuration in which when the measurement result of the first temperature measuring section 90 exceeds the upper limit value, the first valve 11 is closed and the exhaust valve 81 is left open so that hot water in the cleaning tank 2 is immediately exhausted.

Furthermore, an example using the branch conduit 60, the first valve 11, the second valve 62 and the third valve 63 has been described in the above described embodiment, but a three-way valve may be disposed instead of these components.

Furthermore, diluted chemical generation processing is performed every time cleaning disinfecting processing is performed in the above described embodiment, but a diluted chemical may be repeatedly used.

The present invention is not limited to the aforementioned embodiments, but can be modified as appropriate within the range not departing from the spirit and scope or thought of the invention that can be read from the claims of the invention and the entire specification, and such a modified endoscope cleaning/disinfecting apparatus and endoscope cleaning/disinfecting method will also be included in the technical scope of the present invention.

What is claimed is:

1. An endoscope cleaning/disinfecting method using an endoscope cleaning/disinfecting apparatus which comprises:
   a first conduit connected to a hot water supply source that supplies hot water, the hot water having a temperature that is controlled so as to fall within a predetermined specified temperature range that is 20° C. or above;
   a branch conduit that branches off from the first conduit in two directions;
   a cleaning tank that can accommodate the endoscope;
   a dilution tank that mixes the hot water and a chemical to obtain a diluted chemical;
   a second conduit that connects one end of the branch conduit and the cleaning tank;
   a third conduit that connects the other end of the branch conduit and the dilution tank;
   a branch selection section that can select a state of the branch conduit from among a state in which the first conduit is in communication with the second conduit, a state in which the first conduit is in communication with the third conduit and a state in which the second conduit is in communication with the third conduit; and
   a first temperature measuring section that measures a temperature of the liquid introduced into the cleaning tank via the second conduit,
the method comprising:
   a step of introducing the hot water into the cleaning tank in a state in which the first conduit is in communication with the second conduit;
   a step of waiting within a predetermined time until a measurement result of the first temperature measuring section falls within the predetermined specified temperature range in a state in which the hot water is introduced into the cleaning tank;

a step of causing the first conduit to communicate with the third conduit after the measurement result of the first temperature measuring section falls within the predetermined specified temperature range, introducing the hot water into the dilution tank and generating the diluted chemical;

a step of performing at least one of displaying a warning, outputting a warning sound, and stopping the introducing of the hot water into the cleaning tank when the measuring result of the first temperature measuring section does not fall within the predetermined specified temperature range after an elapse of the predetermined time in the state in which the hot water is introduced into the cleaning tank;

a step of exhausting the hot water from the cleaning tank; and a step of transferring the diluted chemical from the dilution tank to the cleaning tank after the step of exhausting the hot water from the cleaning tank, and performing at least one of cleaning processing and disinfecting processing with respect to the endoscope.

2. The endoscope cleaning/disinfecting method according to claim 1, further comprising:

a step of rinsing the interior of the cleaning tank with the hot water after the step of introducing the hot water into the cleaning tank in a state in which the first conduit is in communication with the second conduit;

wherein the step of transferring the diluted chemical from the dilution tank to the cleaning tank and performing at least one of cleaning processing and disinfecting processing with respect to the endoscope is performed after the step of rinsing the interior of the cleaning tank with the hot water.

* * * * *